United States Patent [19]

Iyer

[11] Patent Number: 5,387,352
[45] Date of Patent: Feb. 7, 1995

[54] PHOSPHORUS-CONTAINING COMPOSITIONS

[75] Inventor: Ramnath N. Iyer, Chesterfield, Mo.

[73] Assignee: Ethyl Corporation, Richmond, Va.

[21] Appl. No.: 157,462

[22] Filed: Nov. 26, 1993

[51] Int. Cl.⁶ .......................................... C10M 137/00
[52] U.S. Cl. .................. 252/32.5; 252/49.9; 558/162
[58] Field of Search ............... 558/162; 252/32.5, 49.9

[56] References Cited

U.S. PATENT DOCUMENTS

| | | | |
|---|---|---|---|
| 2,520,090 | 8/1950 | Barrett | 585/162 X |
| 3,318,811 | 5/1967 | Conradi | 252/49.9 |
| 3,987,008 | 10/1976 | Stackman | 260/45.95 D |

*Primary Examiner*—Stephen Kalafut
*Assistant Examiner*—Cephia D. Toomer
*Attorney, Agent, or Firm*—John F. Sieberth

[57] ABSTRACT

Novel aromatic polyphosphate ester-acids and amine salts thereof are described. These products are eminently useful as ashless antiwear agents in lubricating oils.

70 Claims, No Drawings

PHOSPHORUS-CONTAINING COMPOSITIONS

TECHNICAL FIELD

This invention relates to novel and useful aromatic polyphosphate-ester acids, to novel and useful salts of such acid-esters, and to the use of such acid-esters and salts as lubricant additives.

BACKGROUND

For various lubricant and functional fluid applications, there is a need for ashless (i.e., metal-free) antiwear/extreme pressure agents that can supplant conventionally used metal-containing antiwear/extreme pressure agents such as the metal salts of dialkyl dithiophosphoric acids. For decades such metal salts, especially the widely-used zinc salts, have been regarded as among the most useful compounds for this purpose. Thus countless millions of pounds of lubricants, such as gear oils and crankcase lubricating oils for passenger cars, trucks, buses, etc., have been used. Similarly, huge quantities of functional fluids, such as transmission fluids, hydraulic fluids and the like, have utilized metal dialkyl dithiophosphate antiwear/extreme pressure agents, especially the zinc dialkyl dithiophosphates.

For several reasons, including ecological, conservational and performance reasons, a need has arisen for metal-free additives capable of serving as effective replacements for the metal dialkyl dithiophosphates.

This invention is deemed to fulfill this need in an effective, efficient and economical manner.

THE INVENTION

Provided by this invention is a class of aromatic polyphosphate ester-acids and salts thereof. The ester-acids can be represented by the formula:

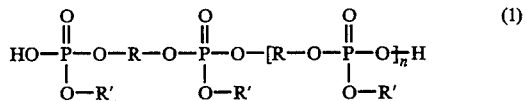

where R is a phenylene group (which may be an o- or p-phenylene group, but preferably is a m-phenylene group), R' is a monovalent hydrocarbyl group, and n is a numeral in the range of from 0 to 5, both inclusive. Preferably R' is an aliphatic hydrocarbyl group containing up to about 30 carbon atoms, and most preferably from about 4 to about 18 carbon atoms. When n is 0, the compound is a benzene diol bis(monohydrocarbyl acid phosphate). When n is greater than 0, the ester-acid can be either a single compound (in which case n is a whole number) or a mixture of compounds (in which case n represents an arithmetical average for the mixture, and thus is either a whole or fractional number).

When produced by the phosphoryl trihalide process described hereinafter, the ester-acids of this invention typically comprise a mixture enriched in a benzene diol bis(monohydrocarbyl acid phosphate), such as products in which about 60 to about 70 wt % of the mixture is a benzene diol bis(monohydrocarbyl acid phosphate) and the balance of the ester-acid mixture is in essence one or more oligomers of the above formula where n is greater than zero. It is conceivable, though unlikely, that the ester-acid product formed may also contain small amounts (e.g., less than 5% by weight) of diaryl-monohydrocarbyl phosphate of the formula:

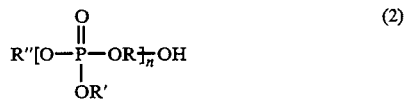

where R'' is a hydroxyaryl group, and R, R' and n are as defined above.

In Formulas (1) and (2) above, the phenylene group, R, can be substituted with 1 to 4 hydrocarbyl substituents, although most preferably the phenylene group is an unsubstituted phenylene group. Such substituents can range from lower alkyl or alkenyl groups (viz., alkyl groups of 1 to about 6 carbon atoms or alkenyl groups of 2 to about 6 carbon atoms) up to long chain hydrocarbyl groups having 300 or more carbon atoms such as alkyl or alkenyl groups derived from polypropenes, polybutenes, polyisobutenes, polyamylenes, copolymers of ethylene and propylene, copolymers of ethylene and butene, copolymers of ethylene and isobutene, copolymers of propene and isobutene, copolymers of propene, butene and isobutene, and the like, having number average molecular weights of up to about 3000 or more. The substituent(s) can also be cycloalkyl or cycloalkenyl groups, aryl groups, aralkyl groups, polyunsaturated aliphatic hydrocarbyl groups, or the like. The number of substituents present on the phenylene group will to some extent be dependent upon steric factors such as the size of the substituent, the configuration of the phenylene group (i.e., whether it is an o-, m-, or p-phenylene group) and the position of the substituent on the phenylene ring. When substituted, the phenylene group will usually have one or two substituents, most often just one.

The non-metallic salts of the acid-esters of Formula (1) above can be quaternary ammonium salts or phosphonium salts. However, the preferred salts of this invention are amine salts, particularly the salts formed by neutralizing the compounds of Formula (1) above with a primary or secondary amine, most preferably a primary amine.

The preferred amine salts of this invention can be depicted by the following Formulas (3) and (4):

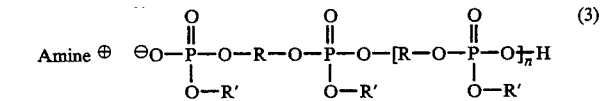

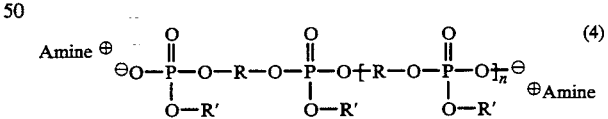

where R, R' and n have the same meanings as in Formula (1) above, and where "Amine⊕" is a protonated amine. Formula (1) depicts an amine salt in which only one of the acid groups has been neutralized by the amine. In Formula (3) both acid groups have been neutralized by the amine. Mixtures of compounds (3) and (4) in any and all proportions form still another embodiment of this invention.

Aliphatic, cycloaliphatic, aromatic, or heterocyclic amines can be used in forming the foregoing amine salts as long as the amines contain at least one primary, secondary or tertiary amino group capable of forming a salt with an acid of Formula (1) above.

The oil-soluble or stably oil-dispersible compounds of Formulas (1) and (2) above and the oil-soluble or stably oil dispersible non-metallic salts of Formula (1) are useful as additives to oils of lubricating viscosity. For example, the oil-soluble or stably oil-dispersible compounds of Formula (1) above are effective antiwear/extreme pressure agents when utilized at suitable concentrations in natural or synthetic lubricating oils. Likewise the oil-soluble or stably oil-dispersible amine salts of Formulas (3) and (4)—which are preferably aliphatic primary or secondary amine salts and more preferably aliphatic primary amine salts—are useful as multipurpose additives for use in oils of lubricating viscosity, especially as antiwear/extreme pressure additives, rust inhibitors and copper passivators. In addition, the amine salts have dispersancy properties. Thus another embodiment of this invention is the provision of oleaginous compositions (lubricating oils and oil-based functional fluids) containing the novel and useful compounds of this invention.

When the ester-acids of Formula (1) above are employed in finished lubricating oils or in additive concentrates (often called "additive packages") which are used in forming finished lubricants, it is preferable that the finished lubricant or concentrate contain a basic nitrogen-containing ashless dispersant such as a basic nitrogen-containing succinimide, a basic nitrogen-containing succinic ester-amide, a basic nitrogen-containing Mannich base dispersant, or a basic nitrogen-containing polymeric dispersant-viscosity index improver, as the presence of such basic nitrogen-containing ashless dispersant enhances the oil solubility of the ester-acid, perhaps by chemical interaction in situ between the acid functionality the ester-acid and the basic nitrogen functionality of the ashless dispersant.

Metal salts of the acid-esters of Formula (1) above are also useful as additives for oils of lubricating viscosity to provide detergency and thermal stabilization properties to the lubricant or functional fluid. For this utility, it is preferred to employ the alkali or alkaline earth metal salts of the acid esters of Formula (1) above, although effective use can also be made of such other metal salts as the aluminum, zinc, manganese, cobalt, iron, copper, nickel, molybdenum, and the like. The non-metallic salts, particularly the amine salts, are preferred however because of their ashless properties and their more environmentally-friendly character.

The above and other features and embodiments of the invention will become still further apparent from the ensuing description and appended claims.

In order to use the salts of this invention as oil additives, the overall product should be soluble or at least stably dispersible in the oil in an amount equivalent to at least 20 ppm (by weight) of phosphorus at 25° C. Thus if short chain amines are used in forming the salt, the R' group(s) of Formulas (3) and (4) above should have sufficient chain length or appropriate structure, and/or the phenylene group(s), R, should be substituted by substituents of sufficient chain length or appropriate structure to render the overall salt soluble or stably dispersible to a level of at least 20 ppm (by weight) of phosphorus in the particular oil being used. As regards "appropriate structure", compounds with aliphatic substituents tend to have enhanced solubility in highly paraffinic oils, compounds with cycloaliphatic substituents tend to have enhanced solubility in highly cycloparaffinic oils, and compounds with aromatic substituents tend to have enhanced solubility in highly aromatic oils, although of course as in any generalization, there can be exceptions to the general rule.

For convenience, the term "oil-soluble" as applied to the aromatic polyphosphate ester-acids of Formula (1) above and the salts thereof such as those of Formulas (3) and (4) above means that the compounds can be dissolved or be stably dispersed in an oil of lubricating viscosity in an amount equivalent to at least 20 ppm (by weight) of phosphorus at 25° C. Preferably the compounds have a substantially higher solubility or stable dispersibility in oil than this, but they need not dissolve or be stably dispersible in the oil in all proportions.

With the foregoing considerations in mind, the aliphatic amines that are suitable for use in forming amine salts of this invention include compounds having one or more amino groups in the molecule, provided that the compound has at least one amino group capable of forming a salt with the ester-acid of Formula (1) above. Monoamines are preferred. The amines, whether monoamines or polyamines, can be and preferably are hydrocarbyl amines although they can contain one or more suitable substituents such as ether oxygen atoms (—O—), hydroxyl groups (—OH), thioether sulfur atoms (—$S_n$—), mercapto groups (—SH), halogen atoms (—X), keto groups (>CO), thioketo groups (>CS), carboxyl groups (—COOH), ester groups (—COOR), nitrilo groups (—CN), thiocyano groups (—SCN), nitro groups (—$NO_2$), hetero nitrogen atoms (—N=), and the like, provided that each substituted hydrocarbyl group of the amine retains its predominantly hydrocarbonaceous character. When substituted amines are used, they preferably have one or more ether oxygen linkages, one or more thioether linkages, one or more hetero nitrogen atoms and/or one or more hydroxyl groups.

Illustrative monoamines and polyamines which may be employed in forming the amine salts of this invention include such as butylamine, 2-ethylhexylamine, octylamine, undecylamine, laurylamine, stearylamine, oleylamine, linoleylamine, linolenylamine, eleostearylamine, cyclopentylamine, cyclohexylamine, 1-amino-4-methylcyclohexane, 1-amino-(2,6-dimethylcyclohexane, 2-aminonorbornane, 4-aminocyclohexene, benzylamine, aniline, o-, m- and/or p-toluidine, 8-amino-1-octyne, diisopropylamine, dihexylamine, N-methyl-N-amylamine, bis(ethylcyclohexyl)amine, N-octyl-N-cycloheptylamine, tributylamine, octyl-N,N-dimethylamine, tetraaminoneopentane, ethanolamine, diethanolamine, triethanolamine, propanolamine, trishydroxyaminomethane, 2-(2-aminoethylamino)-ethanol, 2-[2-(2-aminoethylamino)-ethylamino]-ethanol, 1-(β-aminoethyl)-2-imidazolidone, N,N'-di-β-aminoethyl)imidazolidone-2, 2-(2-aminoethylamino)-5-nitropyridine, 3-amino-N-ethylpiperidine, 2-(2-aminoethyl)-pyridine, 5-aminoindole, 3-amino-5-mercapto-1,2,4-triazole, N-aminoethyl piperazine, N,N'-bis(aminoethyl)piperazine, N,N'-bis(piperazinyl) ethane, 4-(aminomethyl)-piperidine, ethylenediamine, 1,2-propylenediamine, 1,3-propylenediamine, methylaminopropylenediamine, dipropylenetriamine, di-(1,2-butylene)triamine, N-(2-aminoethyl)-1,3-propanediamine, hexamethylenediamine, N-(β-cyanoethyl)ethane-1,2-diamine, 1,3,6,9-tetraaminooctadecane, 1,3,6-triamino-9-oxadecane, N-methyl-1,2-propanediamine, tetra-(1,2-propylene)pentamine, diethylenetriamine, triethylenetetramine, tetraethylenepentamine, pentaethylenehexamine, adenine, guanine, cytosine, guanidine, aminoguanidine, guanylurea, 2,2-diethoxyethylamine, 2,2-dimethoxyethylamine, 4,4-diethoxybutyl amine, 2-amino-1-butanol, 4-amino-1-butanol, butyl 12-aminododecanoate, N-(2-aminoethyl)-piperidine, 2-amino-2-ethyl-1,3-propanediol, N-(2-aminoethyl)-pyrrolidine, o-, m- and/or p-aminoacetophenone, 5-aminoacenaphthene, 1-aminoanthraquinone, 2-aminoanthraquinone, p-phenylazoaniline, aminothiophenol, 2-aminobenzophenone, 4-aminobenzophenone, o-aminobenzyl alcohol, 2-aminofluorene, 2-amino-9-fluorenone, 4-amino-9-fluorenone, N-aminohomopiperidine, 4-aminoantipyrine, 4-amino-2,1,3-benzothiadiazole, 2-aminobenzothiazole, 3-amino-4-carbethoxypyrazole, 2-amino-5,6-dimethylbenzimidazole, 1-amino-2,6-dimethylpiperidine, 2-amino-4,6-dimethylpyridine, 2-amino-4,6-dimethylpyrimidine, 3-amino-5,6-dimethyl-1,2,4-triazole, 6-amino-1,3-dimethyluracil, N-(2-aminoethyl)-morpholine, 3-amino-N-ethylpiperidine, 2-(2-aminoethyl)-pyridine, and the like. It should be apparent from these illustrative compounds that the amines can be aliphatic, cycloaliphatic, aromatic, heterocyclic, aliphatic and cycloaliphatic, aliphatic and aromatic, aliphatic and heterocyclic, cycloaliphatic and aromatic, cycloaliphatic and heterocyclic, aromatic and heterocyclic, etc., in structure; that they may be saturated or contain olefinic, acetylenic and/or aromatic unsaturation; and that they may or may not contain other functional substituents, as long as the compound contains at least one primary, secondary or tertiary amino group capable of forming a salt with an ester-acid of Formula (1) above. Mixtures of suitable amines can be used such as for example commercial mixtures of straight chain, branched chain and cyclic ethylene polyamines having approximate overall compositions falling in the range corresponding to diethylene triamine to pentaethylene hexamine. The salts of this invention can be formed from compounds having combinations of primary and/or secondary and/or tertiary amino groups in the molecule. In general, salts formed from secondary amines, especially aliphatic secondary amines, are preferred and salts formed from primary amines, especially aliphatic primary amines, are particularly preferred.

Also suitable are high molecular weight hydrocarbyl polyamines typically formed by reacting aliphatic or alicyclic polyhalides (or mixture thereof) containing an average of at least about 40 carbon atoms with one or more amines, such as polyalkylene polyamines. Examples of such hydrocarbyl polyamines and the preparation thereof are described in U.S. Pat. Nos. 3,275,554; 3,394,576; 3,438,757; 3,454,555; 3,565,804; 3,671,511; 3,821,302 and in European Patent herein by reference. In general, the hydrocarbyl groups of these hydrocarbyl polyamines typically have a number average molecular weight in the range of about 500–10,000, more usually in the range of about 750–5,000, and often in the range of 1000–2500 and normally are of branched-chain structure, having 0–2 sites of unsaturation. The hydrocarbyl groups are typically derived from petroleum mineral oil, or polyolefins, either homopolymers or higher-order polymers, typically formed from 1-olefins of from 2–6 carbon atoms. such as ethylene, propylene, isobutylene, 1-butene, amylenes, etc., or combinations thereof.

Acylated polyamines having at least one primary or secondary amino group in the molecule can also be used in forming the salts of this invention. These are reaction products of a polyamine typically an polyalkylene polyamine and an acylating agent such as a monocarboxylic acid or polycarboxylic acid, or functional derivatives thereof such as the anhydride, acyl halide or lower alkyl ester thereof. Preferably, the acylated polyamine will contain at least one primary amino group as in the case of alkenyl succinimides and alkenyl succinic esteramides made from polyamines such as ethylene polyamines in proportions relative to the acylating agent such that a substantial amount of free primary amino groups remain in the product mixture. Methods that can be used or adapted for use in forming such acylated compounds are described for example in U.S. Pat. Nos. 3,163,603; 3,184,474; 3,215,707; 3,219,666; 3,271,310; 3,272,746; 3,281,357; 3,306,908; 3,311,558; 3,316,177; 3,340,281; 3,341,542; 3,346,493; 3,381,022; 3,399,141; 3,415,750; 3,433,744; 3,444,170; 3,448,048; 3,448,049; 3,451,933; 3,454,607; 3,467,668; 3,522,179; 3,541,012; 3,542,678; 3,574,101; 3,576,743; 3,630,904; 3,632,510; 3,632,511; 3,697,428; 3,725,441; 3,804,763; 3,836,471; 3,862,981; 3,868,330; 3,936,480; 3,948,800; 3,950,341; 3,957,854; 3,957,855; 3,991,098; 4,071,548; 4,173,540; 4,234,435; and Re. 26,433, the disclosures of which are incorporated herein by reference.

Another category of amines that can be used in forming the amine salts of this invention are the Mannich bases formed from a phenolic compound, an aldehyde (preferably formaldehyde) and a polyamine provided that the Mannich base so formed contains at least one secondary amino group, and more preferably at least one primary amino group which most preferably is positioned on the terminal carbon atom of the polyamine. Examples of Mannich bases formed from polyamines are described in the following U.S. Pat. Nos., the disclosures of which are incorporated herein by reference: 2,459,112; 2,962,442; 2,984,550; 3,036,003; 3,166,516; 3,236,770; 3,368,972; 3,413,347; 3,442,808; 3,448,047; 3,454,497; 3,459,661; 3,493,520; 3,539,633; 3,558,743; 3,586,629; 3,591,598; 3,600,372; 3,634,515; 3,649,229; 3,697,574; 3,703,536; 3,704,308; 3,725,277; 3,725,480; 3,726,882; 3,736,357; 3,751,365; 3,756,953; 3,793,202; 3,798,165; 3,798,247; 3,803,039; 3,872,019; 3,980,569; and 4,011,380.

The number of carbon atoms in any given amine is largely immaterial as long as the salt of the ester-acid is stable under ambient conditions and, when used as an oil additive, the salt is "oil-soluble" as herein defined. The most preferred amines are the hydrocarbyl primary monoamines in which the hydrocarbyl group is an alkyl group, or an ethylenically unsaturated acyclic group having from 1 to 3 olefinic double bonds, wherein the alkyl or ethylenically unsaturated acyclic group has from 8 to 30, and still more preferably 9 to 20 carbon atoms. Highly suitable mixtures amines of these types are available commercially. such as Primene® 81-R amines (a mixture of $C_{12}$ to $C_{14}$ tertiary alkyl primary amines; Rohm & Haas Company), Primene JM-T amine (a tertiary alkyl amine mixture of higher molecular weight), and technical grades of so-called oleylamine.

There are several synthesis routes by which the compounds of this invention can be prepared. One such method involves forming a monohydrocarbyl phosphoryl dihalide, reacting the same with a benzene diol in proportions to form a benzene diol bis(monohydrocarbyl phosphoryl monohalide), hydrolyzing the monohalide to form the benzene diol bis(monohydrocarbyl phosphate), and when forming the salts of this invention, reacting such phosphate with the appropriate base, such as an amine. These operations are typically conducted as follows:

Step 1). To form the monohydrocarbyl phosphoryl dihalide, it is desirable to add a monohydric alcohol or a monohydric phenolic compound to a phosphoryl trihalide, such as phosphoryl trichloride, in molar proportions of 1 mole of the alcohol or phenolic compound to 1 to 1.1 moles of phosphoryl trihalide while maintaining the temperature of the stirred mixture in the range of 0° to 25° C., preferably 10° to 20° C., during the addition period which is typically 1 to 3 hours. Following the addition, the stirred reaction mixture is maintained at 40° to 80° C. for 1 to 3 hours. This reaction can be conducted in bulk, or it can be conducted in an inert liquid solvent such as a paraffinic or aromatic solvent such as toluene, xylene, naphtha, petroleum ether, heptane, octane, and in general any inert liquid hydrocarbon that boils above 100° C. and preferably below 200° C. Most preferably the solvent is one that forms an azeotrope with water. The reaction is usually conducted at atmospheric pressure and desirably the reaction mixture is maintained under an inert atmosphere such as a continuous sweep of nitrogen or other inert gas Step 2). The benzene diol bis(monohydrocarbyl phosphoryl monohalide) is formed by reacting 1.9 to 2 moles of the monohydrocarbyl phosphoryl dihalide from step 1) with 1 mole of a benzene diol such as resorcinol. This reaction is preferably conducted in an inert solvent such as a solvent referred to in step 1) using a Lewis acid catalyst, preferably aluminum chloride at the level of about 0.01 mole percent based on the amount of phosphoryl trihalide used in step 1). The diol is added with stirring to the bis(monohydrocarbyl phosphoryl monohalide) and the reaction temperature is kept at 90° to 110° C., preferably 95° to 105° C., for 3 to 6 hours while maintaining a continuous flow of nitrogen through the system.

Step 3). To form the ester-acid of this invention, the benzene diol bis(monohydrocarbyl phosphoryl monohalide) from step 2) is hydrolyzed by adding an excess of water to the product from step 2) while agitating and maintaining a nitrogen flow over the mixture. The water is added portionwise during a period of 5 to 60 minutes and the temperature is held at 25° to 50° C., preferably 35° to 45° C. The mixture is stirred under nitrogen for up to 3 hours to ensure completion of the hydrolysis. The agitation is then discontinued to allow the organic and aqueous phases to separate. The aqueous layer is drained from the bottom of the reactor, and the ester-acid product solution is washed at least twice with water, and each time the water is drained off.

Step 4). The amine salt of this invention is formed by reacting the ester-acid of step 3) with the requisite quantity of amine. This can be done either by distilling off the wet inert solvent from the ester-acid, charging fresh dry inert solvent to the ester-acid, and then adding the amine to form the salt, or by adding the amine to the ester-acid solution and then distilling off the wet inert solvent from the amine salt. In either case the salt is of Formula (3) and/or (4), depending upon the stoichiometry utilized in step 4).

The following examples, wherein all parts and percentages are by weight unless otherwise specified, are illustrative of the compounds of this invention and the production thereof by the above-described process steps. These examples are not intended to limit, do not limit, and should not be construed as limiting, the practice of the generic aspects of this invention.

EXAMPLE 1

1,3-Benzenediol bis(octylphosphate) and the bis oleyl amine salt thereof

Step 1. Preparation of n-Octyl Phosphorodichloridate

Phosphoryl trichloride (3113 g; 20.3 moles) is placed in a 5-liter flask fitted with a condenser and mechanical stirrer, and cooled down to about 10° C. (external ice bath). Octanol (2380 g; 18.3 moles; 0.9 equivalents with respect to $POCl_3$) is added at a rate such that the reaction temperature remains below 15° C. The reaction is exothermic and the HCl gas that evolves during this reaction is vented out with a flow of nitrogen through an aspirator operated with a slight vacuum of about 0.5 inches of mercury. When addition of alcohol is completed (2–3 hours), the ice bath is removed and the reaction mixture is allowed to warm to room temperature and then warmed to 60°–70° C. and stirred at this temperature for 1.5 hours to drive out most of the HCl gas. The product, octyl phosphorodichloridate, is obtained as a clear light yellow free-flowing liquid.

Step 2. Preparation of Resorcinol bis(octylphosphorodichloridate)

The product from Step 1 is transferred to a 22 liter reactor. and toluene (7000 g) is added thereto. Then $AlCl_3$ (28 g; 0.21 mole; 0.01 molecular equivalent with respect to $POCl_3$) and resorcinol (1007 g; 9.15 moles; 0.5 molecular equivalent with respect to n-octanol) are charged to the reactor. The sides of the flask are washed with a further 1600 g of toluene bringing the total toluene content to 8600 g. The reaction mixture is heated to 100° C. The reaction mixture becomes a clear solution at 50°–60° C. and starts turning into a greenish red solution at about 90° C. The reaction mixture is held at 95°–100° C. for 5 hours and allowed to cool back to room temperature. The product produces a green solution in toluene. Infrared shows characteristic P-Cl stretches in the 550–650 $cm^{-1}$ region.

Step 3. Hydrolysis of Resorcinol bis(octylphosphorodichloridate) to Resorcinol bis(octylphosphate)

Water (1800 g; 100 moles; approximately 5 equivalents with respect to $POCl_3$) is added in increments to the greenish-red reaction mixture. The reaction is moderately exothermic and the rate of addition is controlled so as to keep the temperature of the reaction mixture below 50° C. in order to prevent the possible hydrolysis of the —OR group. (Alternatively, the reaction mixture can be cooled externally). After the water addition is completed, the reaction mixture is stirred for an hour. Then stirring is discontinued and the mixture is allowed to stand to enable an aqueous phase to separate from the organic layer. The dark red water layer is separated and washed 8 times with 1 liter portions of water. The water layer becomes lighter progressively and the last three washings tend be essentially colorless. The separation into the aqueous and organic layers occurs efficiently. The toluene solvent and residual water is boiled off under reduced pressure, the residual water coming off as an azeotrope of toluene during the distillation. The product is obtained as a greenish red viscous liquid in about 80–85% yield with respect to resorcinol. NMR indicates the formation of resorcinol bis(octylphosphate) along with higher molecular weight oligomers. The product is a green viscous liquid that also displays a red color depending upon the angle of viewing. Typically, the product contains in the range of 9–11.5% phosphorus (theoretical %P=12.55).

Step 4. Conversion of phosphate ester-acid to amine salt of phosphate.

A portion of the product from Step 3 (1591 g) is dissolved in 3000 g of toluene. A charging funnel is charged with oleyl amine (Armeen ® OL; Akzo Chemical) (1724 g; 6.44 moles; approximately 2 equivalents of the amine with respect to the theoretical amount of ester-acid present) is added with stirring and frequent monitoring of the pH. The initial pH of the reaction mixture is less than 2. The addition is slightly exothermic and the temperature rises to maximum of approximately 40° C., and then slowly decreases with further addition of the amine. The pH is monitored by withdrawing approximately 2 mL of the reaction mixture and dissolving the same in 50 mL of 1:1 toluene/methanol solvent and measuring the pH of this solution with a standard pH meter. The amine is added until the pH of the solution remains constant at 7.9 (typically a total of about 1620 g of the amine is required) The clear amber viscous liquid becomes buttery yellow on cooling. Typically, the phosphorus content of the product is somewhat below the theoretical value of 6.01% P).

EXAMPLE 2

The bis $C_{12}$-$C_{14}$ tertiary alkyl primary amine salt of 1,3-Benzenediol bis(octylphosphate)

A 133.21 g portion of the ester-acid from Step 3 of Example 1 dissolved in 200 g of toluene is neutralized with 84.88 g of $C_{12}$-$C_{14}$ tertiary alkyl primary amine (Primene ® 81-R; Rohm & Haas) dissolved in 71 g of toluene as in Step 4 of Example 1. The final constant pH of the reaction mixture is typically approximately 8. The product is a clear red viscous liquid which contains somewhat less than the theoretical amount of phosphorus (7.01%)

EXAMPLE 3

1,3-Benzenediol bis(pentylphosphate)

Using the general procedure of Steps 1–3 of Example 1, resorcinol bis(pentylphosphate) is prepared from $POCl_3$ (289.3 g; 1.9 moles), n-pentanol (150.5 g; 1.71 moles), toluene (800 g) , $AlCl_3$(2.6 g; 0.019 moles), and resorcinol (93.5 g; 0.85 moles).

EXAMPLE 4

The his N,N-dimethylhexadecyl amine salt of 1,3-Benzenediol bis(pentylphosphate)

Using the general procedure of Step 4 of Example 1, resorcinol bis(pentylphosphate) (22.5 g; 0.055 mole) formed as in Example 3 in 45 mL of toluene is neutralized with a solution of 30.4 g (0.11 mole) of N,N-dimethylhexadecylamine (Armeen ® DM16D; Akzo Chemical) dissolved in 30 mL of toluene. The final pH is approximately 7.5. The solvent is removed by distillation. The product is a waxy yellow product which typically contains somewhat less than the theoretical quantity of phosphorus.

EXAMPLE 5

The bis octadecyl amine salt of 1,3-Benzenediol bis(pentylphosphate)

Octadecyl amine (Armeen ® 18D) is slowly added to a solution of 25.0 g (0.06 mole) of the ester-acid formed as in Example 3 dissolved in 80 mL of toluene. The reaction mixture gradually changes from a green color to a reddish color. This reaction is only mildly exothermic. When a total of about 28.4 g of the amine has been added, the pH of the solution is approximately 8.2. Unreacted solids are filtered from the reaction product and after distilling off the solvent, approximately 54 g of the amine salt is recovered. The product on cooling solidifies to a waxy solid which typically contains somewhat less than the theoretical quantity of phosphorus.

EXAMPLE 6

The bis N,N-dimethyloctadecyl amine salt of 1,3-Benzenediol bis(pentylphosphate)

Using the general procedure of Step 4 of Example 1, resorcinol bis(pentylphosphate) (26 g; 0.063 mole) formed as in Example 3 in 60 mL of toluene is neutralized with a solution of 36.5 g of N,N-dimethyloctadecylamine (Armeen ® DM18D; Emery Industries) dissolved in 40 mL of toluene. The final pH of the reddish-pink viscous reaction mixture is approximately 7.3. The solvent is removed by distillation. The product is a waxy solid which typically contains somewhat less than the theoretical quantity of phosphorus.

EXAMPLE 7

The bis $C_{16}$-$C_{22}$ tertiary alkyl primary amine salt of 1,3-Benzenediol bis(pentylphosphate)

Resorcinol bis(pentylphosphate) (20.67 g; 0.05 mole) formed as in Example 3 in 40 mL of toluene is neutralized with a solution of 34 g of $C_{16}$-$C_{22}$ tertiary alkyl amine (Primene ® JM-T amine; Rohm & Haas) dissolved in 34 mL of toluene, using the general procedure of Step 4 of Example 1. The final pH of the yellowish-green-red reaction mixture is approximately 8.2. The solvent is removed by distillation. The product is a viscous red liquid. It typically contains approximately 4.9% phosphorus as compared to a theoretical value of 5.8%.

EXAMPLE 8

1,2-Benzenediol bis(octylphosphate)

Step 1. Preparation of n-Octyl Phosphorodichloridate

Phosphoryl trichloride (300 mL; 3.22 moles) is placed in a 2-liter flask fitted with a condenser and mechanical stirrer, and cooled down to about 10° C. (external ice bath). Octanol (377.3 g; 2.9 moles) is added dropwise while maintaining a continuous flow of nitrogen into the $POCl_3$ and through the reaction system at a rate such that the reaction temperature remains below 15° C. The reaction is exothermic and the HCl gas that evolves during this reaction is vented out with an aspirator. When addition of alcohol is completed (2–2.5 hours), the ice bath is removed and the reaction mixture is allowed to warm to room temperature and then warmed to approximately 40°–55° C. and stirred at these temperatures for 2.25 hours while continuing the nitrogen strip to drive out most of the HCl gas. The product remaining in the flask is approximately 700 grams of octyl phosphorodichloridate.

Step 2. Preparation of Catechol bis(octylphosphorodichloridate)

A portion of the product from Step 1 (100 g) is transferred to a 1-liter flask, and toluene (100 mL) is added thereto. Then AlCl$_3$ (0.65 g) and catechol (22.5 g; 0.2 mole; 0.5 molecular equivalent with respect to n-octanol) are charged to the reactor. The sides of the flask are washed with a further 150 mL of toluene bringing the total toluene content to 250 mL. The reaction mixture is heated to 100° C. for 5 hours, and then allowed to cool to room temperature.

Step 3. Hydrolysis of Catechol bis(octylphosphorodichloridate) to Catechol bis(octylphosphate)

Water (120 g) is added dropwise to the product of Step 2 over a ten minute period with stirring. The reaction is moderately exothermic and the temperature rises from about 22° C. to about 38° C. during this period. After stirring for one hour, the contents of the flask are transferred to a separating funnel and washed successively with eight 50-mL portions of water, and each time the water layer is drained off. The hydrolyzed mixture is allowed to stand for 12 hours, after which a further small amount of water is drained off. The solvent is then stripped off at reduced pressure to yield approximately 80 grams of the catechol bis(octylphosphate), a reddish brown liquid. $^{31}$P NMR confirms the existance of the desired product.

EXAMPLE 9

1,4-Benzenediol bis(octylphosphate)

Step 1. Preparation of Hydroquinone bis(Octyl Phosphorochloridate)

n-Octyl phosphorodichloridate (79.25 g; 0.32 mole) prepared as in Example 8 is dissolved in 100 mL of toluene. Then AlCl$_3$ (0.5 g) and hydroquinone (17.7 g; 0.16 mole) are charged to the reactor. The sides of the flask are washed with a further 100 mL of toluene bringing the total toluene content to 200 mL. The reaction mixture is heated to 95°–105° C. for 2.5 hours, and then allowed to cool to room temperature.

Step 2. Hydrolysis of Hydroquinone bis(octylphosphorochloridate) to Hydroquinone bis(octylphosphate)

Water (120 g) is added dropwise to the product of Step 1 over a ten minute period with stirring. The reaction is moderately exothermic and the temperature rises from about 22° C. to about 38° C. during this period. The suspension is stirred for one hour and allowed to stand for 48 hours. The contents of the flask are transferred to a 500 mL separatory funnel and stirred with a mixture of water and toluene, and warmed slightly. On shaking the separatory funnel, the white solids appears to go into solution or suspension partly at the water-toluene interface. The organic layer is washed 5 times with 125-mL portions of water, and each time the water layer is drained off. The hydrolyzed mixture is allowed to stand for 12 hours. The solvent is then stripped off at reduced pressure to yield a slightly viscous amber liquid in approximately a 75–80% yield.

EXAMPLE 10

1,3-Benzenediol bis(pentylphosphate) and the bis oleyl amine salt thereof

Step 1. Preparation of n-Pentyl Phosphorodichloridate

Phosphoryl trichloride (306 g; 2 moles) is placed in a 2-liter flask fitted with a condenser and mechanical stirrer, and cooled down to about 10° C. (external ice bath). Pentanol (159 g; 1.8 moles; 0.9 equivalents with respect to POCl$_3$) is added at a rate such that the reaction temperature remains below 15° C. The reaction is exothermic and the HCl gas that evolves during this reaction is vented out with a flow of nitrogen using an aspirator operated at a slight vacuum (about 0.5 inches of mercury). When addition of alcohol is completed (about 1.5 hours), the ice bath is removed and the reaction mixture is allowed to warm to room temperature and then warmed to 60°–70° C. and stirred at this temperature for 1.5 hours to drive out most of the HCl gas. The product, pentyl phosphorodichloridate, is obtained as a clear light yellow free-flowing liquid.

Step 2. Preparation of Resorcinol bis(pentylphosphorodichloridate)

To the reaction mixture from Step 1 is added 100 mL tolune. Then AlCl$_3$ (3.1 g; 0.023 mole; 0.01 molecular equivalent with respect to POCl$_3$) and resorcinol (105 g; 0.95 mole; 0.5 molecular equivalent with respect to n-pentanol) are charged to the reactor. The sides of the flask are washed with a further 70 mL of toluene bringing the total toluene content to 1070 mL. The reaction mixture is heated to 100° C. The reaction mixture becomes a clear solution at 50°–60° C. and starts turning into a greenish red solution at about 90° C. The reaction mixture is held at 95°–100° C. for 5 hours and allowed to cool back to room temperature. The product produces a green solution in toluene. Infrared shows characteristic P-Cl stretches in the 550–650 cm$^{-1}$ region.

Step 3. Hydrolysis of Resorcinol bis(pentylphosphorodichloridate) to Resorcinol bis(pentylphosphate)

Water (250 mL; 14 moles; approximately 7 equivalents with respect to POCl$_3$) is added in increments to the greenish-red reaction mixture. The reaction is moderately exothermic and the rate of addition is controlled so as to keep the temperature of the reaction mixture below 50° C. in order to prevent the possible hydrolysis of the —OR group. (Alternatively, the reaction mixture can be cooled externally). After the water addition is completed, the reaction mixture is stirred for an hour. Then stirring is discontinued and the mixture is allowed to stand to enable an aqueous phase to separate from the organic layer. The dark red water layer is separated and washed 9 times with 120 mL portions of water. The water layer becomes lighter progressively and the last three washings tend to be essentially colorless. The separation into the aqueous and organic layers occurs efficiently. The toluene solvent and residual water is boiled off under reduced pressure, the residual water coming off as an azeotrope of toluene during the distillation. The product is obtained as a greenish red viscous liquid in about 80–85% yield with respect to resorcinol. NMR indicates the formation of resorcinol bis(pentylphosphate) along with higher molecular weight oligomers. The product is a green viscous liquid that also displays a red color depending upon the angle of viewing. Typically, this product is formed in a yield of about 65%.

Step 4. Conversion of phosphate ester-acid to amine salt of phosphate

A portion of the product from Step 3 (205.7 g) is dissolved in 400 mL of toluene. A charging funnel is charged with oleyl amine (Armeen ® OL; Akzo Chemical) (240.6 g; 0.90 mole) is added with stirring and frequent monitoring of the pH as in Step 4 of Example 1. The clear amber viscous liquid becomes a dark brown viscous liquid on cooling. Typically, the phosphorus content of the product is somewhat below the theoretical value of 6.6% P, e.g., approximately 5.4% P.

EXAMPLE 11

The bis $C_{12}$-$C_{14}$ tertiary alkyl primary amine salt of 1,3-Benzenediol bis(pentylphosphate)

205 g of product formed as in Steps 1-3 of Example 10 is dissolved in 400 mL of toluene. To this is added 163.8 g of $C_{12}$-$C_{14}$ tertiary alkyl primary amine (Primene® 81-R) dissolved in 190 mL of toluene. The neutralization is conducted as in Step 4 of Example 1. The final constant pH of the reaction mixture is typically approximately 8. The product is a clear red viscous liquid which contains somewhat less than the theoretical amount of phosphorus (7.6%). For example, a typical product may contain approximately 5.6% of phosphorus.

EXAMPLE 12

1,3-Benzenediol bis(decylphosphate) and the his oleyl amine salt thereof

The procedures of Steps 1-4 of Example 1 are repeated using the following amounts of the following materials.

Step 1: Phosphoryl trichloride, 181 g; n-decanol, 151 g.
Step 2: Toluene (initial charge) 500 mL; toluene (wash) 75 mL; ALCl$_3$ 1.5 g; resorcinol 53 g.
Step 3: Water, 100 mL.

Typically the product (resorcinol bis(decylphosphate) is formed in a yield in the range of about 80 to 85%).

Step 4: In this operation, a 70.7 g portion of the product from Step 3 dissolved in 140 mL of toluene is neutralized as in Example 1 with 68.7 g of oleylamine (Kemamine; Azko Chemical).

The final neutralized product is a buttery yellow viscous non-flowable liquid. In one such operation, the product was found to contain 5.7% of phosphorus which generally corresponds to the theoretical content.

EXAMPLE 13

1,2-Benzenediol bis(octylphosphate) and the his oleyl amine salt thereof

These products are prepared substantially as described in Example 1 except that a chemically equivalent quantity of catechol is employed in lieu or resorcinol. The catechol bis(octylphosphorodichloridate) solution in toluene is reddish-green in coloration and shows the characteristic P-Cl stretches in the 550-650 cm$^{-1}$ region. The cathechol bis(octylphosphate) formed in the hydrolysis step is a reddish-brown liquid and typically is formed in a yield of about 80%. NMR indicates the formation of cathechol bis(octylphosphate) along with higher molecular weight oligomers. The oleylamine salt of catechol bis(octylphosphate) after the removal of toluene solvent and water is a buttery yellow viscous liquid at room temperature. Typically, the product will contain approximately 4.6% of phosphorus.

EXAMPLE 14

1,4-Benzenediol bis(octylphosphate) and the his oleyl amine salt thereof

These products are prepared substantially as described in Example 1 except that a chemically equivalent quantity of hydroquinone is employed in lieu of resorcinol. The hydroquinone bis(octylphosphorodichloridate) solution in toluene is amber in color. The hydroquinone bis(octylphosphate) formed in the hydrolysis step is a slightly viscous amber liquid and typically is formed in a yield of about 75%. NMR indicates the formation of hydroquinone bis(octylphosphate) along with higher molecular weight oligomers. The oleyl amine salt of hydroquinone bis(octylphosphate) after the removal of toluene solvent and water is a buttery yellow viscous liquid at room temperature. Typically, the product will contain approximately 4.5% of phosphorus.

Other methods may be used for synthesizing the compounds of this invention. One such method involves reacting a benzene diol with phosphorous acid (H$_3$PO$_3$) to form the benzene diol bis(hydrogen phosphite):

(HO) (H)P(O)-O-R-O-P(O) (H) (OH)

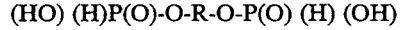

In the second stage, this phosphite is reacted with a monohydric alcohol or phenolic compound to form the benzene diol bis(monohydrocarbyl hydrogen phosphite):

(R'O) (H)P(O)-O -R-O-P(O) (H) (OR')

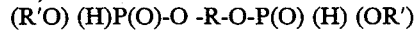

The third stage involves oxidizing the benzene diol bis(monohydrocarbyl hydrogen phosphite) to form the benzene diol bis(monohydrocarbyl acid phosphate):

(R'O) (HO)P(O)-O-R-O-P(O) (OH) (OR')

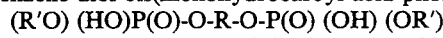

When forming the salts of this invention this ester-acid is reacted with the appropriate base, such as an amine.

A variant of this latter method which is also suitable comprises reacting phosphorous acid (H$_3$PO$_3$) with a monohydric alcohol or phenolic compound proportioned to form a monohydrocarbyl hydrogen phosphite:

(R'O)P(O) (H) (OH)

This phosphite is reacted with a benzene diol in proportions to yield a benzene diol bis(monohydrocarbyl hydrogen phosphite:

(R'O) (H)P(O)-O-R-O-P(O) (H) (OR')

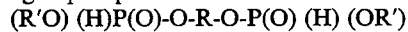

The third stage involves oxidizing the benzene diol bis(monohydrocarbyl hydrogen phosphite) to form the benzene diol bis(monohydrocarbyl acid phosphate):

(R'O) (HO)P(O)-O-R-O-P(O) (OH) (OR')

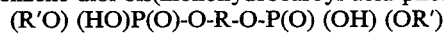

When forming the salts of this invention this ester-acid is reacted with the appropriate base, such as an amine.

An additional method which may be used to produce the compounds of this invention involves reacting a benzene diol with phosphorus pentoxide to produce a benzene diol bis(phosphoric acid);

(HO)$_2$P(O)-O-R-O-P(O) (OH)$_2$

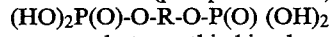

In a second stage, this bis phosphoric acid is reacted with an epoxide such as 1,2-epoxydecane to produce a benzene diol bis(monohydrocarbyl acid phosphate):

(R'O) (HO)P(O)-O-R-O-P(O) (OH) (OR')

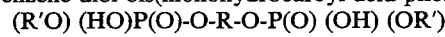

When forming the salts of this invention this ester-acid is reacted with the appropriate base, such as an amine.

Yet another method involves reacting a benzene diol with phosphorus pentoxide to produce a benzene diol bis(phosphoric acid):

(HO)$_2$P(O)-O-R-O-P(O) (OH)$_2$

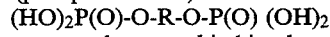

In a second stage, this bis phosphoric acid is reacted with an aryl sulfonic acid such as toluene sulfonic acid, to produce a benzene diol bis(monoarylsulfonyl acid phosphate):

(ArO₂SO) (HO)P(O)-O-R-O-P(O) (OH) (OSO₂Ar)

The third stage involves reacting this acid phosphate with an alcohol or phenolic compound to produce a benzene diol bis(monohydrocarbyl acid phosphate):

(R'O) (HO)P(O)-O-R-O-P(O) (OH) (OR')

When forming the salts of this invention this ester-acid is reacted with the appropriate base, such as an amine.

Still another method involves reacting phosphorus pentoxide with an alcohol or phenolic compound in proportions yielding a monohydrocarbyl phosphate:

(R'O)P(O) (OH)₂

In a second stage this monohydrocarbyl phosphate is reacted with an aryl sulfonic acid such as toluene sulfonic acid, to produce a monohydrocarbyl monoarylsulfonyl acid phosphate:

(R'O)P(O) (OH) (OSO₂Ar)

In the third stage this monohydrocarbyl monoarylsulfonyl acid phosphate is reacted with a benzene diol, typically resorcinol, in proportions to form a benzene diol bis(monohydrocarbyl acid phosphate):

(R'O) (HO)P(O)-O-R-O-P(O) (OH) (OR')

When forming the salts of this invention this ester-acid is reacted with the appropriate base, such as an amine.

The amine salts of this invention can serve a multiplicity of functions when used as additives for lubricating oil and oil-based power transmission fluids. For example the amine salts formed as in Examples 1, 2, 10 and 11 were found to be powerful antiwear agents. Thus four separate blends of mineral oil each containing 60 ppm by weight of phosphorus as one of the respective amine salts of these examples all passed the ASTM D2882 MERCON® pump wear test. These oils also gave excellent results in the 4-ball wear test. In contrast, a commercially-available zinc dialkyldithiophosphate antiwear agent when used in the same base oil at 200 ppm by weight of phosphorus failed the MERCON® pump wear test.

Similarly, amine salts of this invention such as the oleylamine salts can provide excellent antirust protection as measured for example by the ASTM D665B rust test. In this test steel pins are partially immersed in a stirred mixture of test oil and a standard synthetic sea water solution and the mixture is maintained at 60° C. for 24 hours. It was found that a lubricant of this invention containing 60 ppm of phosphorus as an amine salt formed as in Examples 1 and 10 when subjected to this test yielded test pins having no visible rust whatever, and thus passed the test. Zinc dialkyl dithiophosphates cannot provide rust protection sufficient to pass this test.

The extreme pressure properties of lubricants can be markedly improved by use of an amine salt of this invention. For example, a lubricant of this invention containing 60 ppm by weight of phosphorus as a salt formed as in Example 11 was subjected to the FZG extreme pressure test and was found to successfully pass through all 12 load stages of the test without failure. In other FZG tests the same base oil containing the same concentration of phosphorus as the amine salt of Example 10 gave a pass at an average load stage of 11. The untreated oil fails at the 4 to 6 load stages. Moreover, fully formulated lubricants containing 300 ppm by weight of phosphorus as zinc dialkyl dithiophosphate typically fails at the 11 load stage.

Another function which can be fulfilled by use of suitable amine salts of this invention is copper corrosion inhibition. For example mineral oils were blended to contain 60 ppm by weight of phosphorus as one of the respective amine salts formed as in Examples 1, 2, 10 and 11. Each of these four oil compositions of this invention gave a 1b copper rating in the ASTM D130 test procedure.

The ester-acids of this invention are also useful as additives to oils of lubricating viscosity. For example, there effectiveness as antiwear agents is illustrated by the results of standard 4-ball wear test in which the base oil blend consisted of a commercially-available 150 low pour solvent neutral mineral oil containing 0.15 weight % of a boronated Mannich base dispersant (Amoco 9250 additive). Individual portions of this base oil blend additionally containing resorcinol bis(octylphosphate), catechol bis(octylphosphate), and hydroquinone bis(octylphosphate) (formed as in Examples 1, 13, and 14 respectively), at respective concentrations of 80, 83, and 85 ppm of phosphorus gave reductions in 4-ball wear scar diameter of 21.3%, 46.7%, and 33.3%, respectively, as compared to the base oil blend itself.

The ester-acids of this invention are also effective as copper corrosion inhibitors as illustrated by the results of a group of tests performed using the ASTM D130 test procedure. The copper rod exposed during the test to an additive-free 150 low pour solvent neutral mineral oil had a visual rating of 95% 3b and 5% 4a. That is, approximately 95% of the surface of the rod was classified as 3b in appearance and approximately 5% of its surface was even poorer in appearance as it was rated 4a. In contrast, the same oil containing resorcinol bis(octylphosphate) (formed as in Example 1) at a concentration of 0.05 wt % gave a rating of 50% 2c and 50% 2e, and at a concentration of 0.1 wt % gave a rating of 50% 1b and 50% 2e. Similarly, the same base oil containing 0.05 wt % of resorcinol bis(pentylphosphate) (formed as in Example 3) gave a rating of 50% 2c and 50% 2e, whereas at a concentration of 0.1 wt %, gave a rating of 25% 2b, 50% 2c, and 25% 2e.

The acid-esters and the amine salts thereof may also find use as additives for fuels as well as lubricants. Additionally, the acid-esters of the invention may be used as reactive monomers in the preparation of polyester films, fibers and filaments having flame retardant properties.

I claim:

1. An oil-soluble amine salt of a benzenediolbis(monohydrocarbylphosphate) wherein the amine is an aliphatic hydrocarbyl monoamine.

2. An amine salt of claim 1 wherein said monoamine is an aliphatic primary amine having up to 30 carbon atoms in the molecule and in which the aliphatic group of said amine is an alkyl group or an ethylenically unsaturated acyclic group having from 1 to 3 olefinic double bonds.

3. An amine salt of claim 2 wherein said primary amine is a tertiary alkyl primary amine.

4. An amine salt of claim 3 wherein said tertiary alkyl primary amine has about 12 to about 22 carbon atoms in the molecule.

5. An amine salt of claim 4 wherein said tertiary alkyl primary amine has about 12 to about 14 carbon atoms in the molecule.

6. An amine salt of claim 4 wherein said tertiary alkyl primary amine has about 16 to about 22 carbon atoms in the molecule.

7. An amine salt of claim 2 wherein said primary amine is oleyl amine.

8. An amine salt of claim 2 wherein said primary amine is octadecyl amine.

9. An amine salt of claim 1 wherein said monoamine is an aliphatic tertiary amine having up to 30 carbon atoms in the molecule.

10. An amine salt of claim 9 wherein said tertiary amine is hexadecyl dimethyl amine.

11. An amine salt of claim 9 wherein said tertiary amine is octadecyl dimethyl amine.

12. An amine salt of claim 1 wherein said salt is an amine salt of a 1,3-benzenediolbis(monohydrocarbylphosphate).

13. An amine salt of claim 3 wherein said salt is the tertiary alkyl primary amine salt of 1,3-benzenediolbis(monooctylphosphate) wherein the amine is a combination of tertiary alkyl primary amines having about 12 to about 14 carbon atoms in the molecule.

14. An amine salt of claim 2 wherein said salt is the oleyl amine salt of 1,3-benzenediolbis(monooctylphosphate).

15. An amine salt of claim 3 wherein said salt is the tertiary alkyl primary amine salt of 1,3-benzenediolbis(monopentylphosphate) wherein the amine is a combination of tertiary alkyl primary amines having about 16 to about 22 carbon atoms in the molecule.

16. An amine salt of claim 2 wherein said salt is the octadecyl amine salt of 1,3-benzenediolbis(monopentylphosphate).

17. An amine salt of claim 2 wherein said salt is the oleyl amine salt of 1,3-benzenediolbis(monodecylphosphate).

18. An amine salt of claim 1 wherein said salt is the hexadecyl dimethyl amine salt of 1,3-benzenediolbis(monopentylphosphate).

19. An amine salt of claim 1 wherein said salt is the octadecyl dimethyl amine salt of 1,3-benzenediolbis(monopentylphosphate).

20. An amine salt of claim 1 wherein said salt is an amine sale of a 1,2-benzenediolbis(monohydrocarbylphosphate).

21. An amine salt of claim 2 wherein said salt is the oleylamine salt of 1,2-benzenediolbis(monooctylphosphate).

22. An amine salt of claim 1 wherein said salt is an amine salt of a 1,4-benzenediolbis(monohydrocarbylphosphate).

23. An amine salt of claim 2 wherein said salt is the oleylamine salt of 1,4-benzenediolbis(monooctylphosphate)

24. An amine salt of claim 2 wherein said benzenediolbis(monohydrocarbylphosphate) is a 1,3-benzenediolbis(monohydrocarbylphosphate).

25. An amine salt of claim 3 wherein said benzenediolbis(monohydrocarbylphosphate) is a 1,3-benzenediolbis(monohydrocarbylphosphate).

26. An amine salt of claim 2 wherein said benzenediolbis(monohydrocarbylphosphate) is a 1,2-benzenediolbis(monohydrocarbylphosphate).

27. An amine salt of claim 3 wherein said benzenediolbis(monohydrocarbylphosphate) is a 1,2-benzenediolbis(monohydrocarbylphosphate).

28. An amine salt of claim 2 wherein said benzenediolbis(monohydrocarbylphosphate) is a 1,4-benzenediolbis(monohydrocarbylphosphate).

29. An amine salt of claim 3 wherein said benzenediolbis(monohydrocarbylphosphate) is a 1,4-benzenediolbis(monohydrocarbylphosphate).

30. An amine salt of claim 2 wherein said benzenediolbis(monohydrocarbylphosphate) is a benzenediolbis(monoalkylphosphate).

31. An amine salt of claim 30 wherein the amine has 8 to 30 carbon atoms in the molecule.

32. An amine salt of claim 31 wherein the amine has 9 to 20 carbon atoms in the molecule.

33. An amine salt of claim 32 wherein said salt is an oleyl amine salt.

34. A lubricant additive composition which comprises from 0.1 to 99.9 weight percent of at least one oil of lubricating viscosity and from 99.9 to 0.1 weight percent of at least one oil-soluble amine salt of a benzenediolbis(monohydrocarbylphosphate) wherein the amine is an aliphatic hydrocarbylmonoamine.

35. A composition in accordance with claim 34 wherein said oil-soluble amine salt is an oil-soluble amine salt of a 1,2-benzenediolbis(monohydrocarbylphosphate).

36. A composition in accordance with claim 35 wherein said amine salt is an aliphatic primary amine salt of a 1,2-benzenediolbis(monoalkylphosphate).

37. A composition in accordance with claim 34 wherein said oil-soluble amine salt is an oil-soluble amine salt of a 1,4-benzenediolbis(monohydrocarbylphosphate).

38. A composition in accordance with claim 37 wherein said amine salt is an aliphatic primary amine salt of a 1,4-benzenediolbis(monoalkylphosphate).

39. A composition in accordance with claim 34 wherein said oil-soluble amine salt is an oil-soluble amine salt of a 1,3-benzenediolbis(monohydrocarbylphosphate).

40. A composition in accordance with claim 39 wherein said amine salt is an aliphatic primary amine salt of a 1,3-benzenediolbis(monoalkylphosphate).

41. A composition in accordance with claim 34 wherein the monoamine is an aliphatic primary monoamine having 8 to 30 carbon atoms in the molecule and in which the aliphatic group of said monoamine is an alkyl group or an ethylenically unsaturated acyclic group having from 1 to 3 olefinic double bonds.

42. A composition in accordance with claim 41 wherein the monoamine has 9 to 20 carbon atoms in the molecule.

43. A composition in accordance with claim 42 wherein the monoamine is oleyl amine.

44. A composition in accordance with claim 34 wherein the monoamine is a tertiary alkyl primary amine.

45. A composition in accordance with claim 44 wherein the monoamine is a combination of tertiary alkyl primary amines having about 12 to about 14 carbon atoms in the molecule.

46. A composition in accordance with claim 44 wherein the monoamine is a combination of tertiary alkyl primary amines having about 16 to about 22 carbon atoms in the molecule.

47. A composition in accordance with claim 34 wherein said amine salt is an oleyl amine salt of a 1,3-benzenediolbis(monohydrocarbylphosphate).

48. A composition in accordance with claim 47 wherein said 1,3-benzenediolbis(monohydrocarbylphosphate) is 1,3-benzenediolbis(monopentylphosphate).

49. A composition in accordance with claim 47 wherein said 1,3-benzenediolbis(monohydrocarbylphosphate) is 1,3-benzenediolbis(monodecylphosphate).

50. A composition in accordance with claim 47 wherein said 1,3-benzenediolbis(monohydrocarbylphosphate) is 1,3-benzenediolbis(monodecylphosphate).

51. A lubricant composition which comprises a major amount of at least one oil of lubricating viscosity and a minor antiwear/extreme pressure amount of at least one oil-soluble amine salt of a benzenediolbis(monohydrocarbylphosphate) wherein the amine is an aliphatic hydrocarbyl monoamine.

52. A composition in accordance with claim 51 wherein said monoamine is an aliphatic primary amine having up to 30 carbon atoms in the molecule and in which the aliphatic group of said amine is an alkyl group or an ethylenically unsaturated acyclic group having from 1 to 3 olefinic double bonds.

53. A composition in accordance with claim 52 wherein said primary amine is a tertiary alkyl primary amine.

54. A composition in accordance with claim 52 wherein said primary amine is oleyl amine.

55. A composition in accordance with claim 52 wherein said primary amine is octadecyl amine.

56. A composition in accordance with claim 51 wherein said oil-soluble amine salt is an oil-soluble amine salt of a 1,2-benzenediolbis(monohydrocarbylphosphate).

57. A composition in accordance with claim 56 wherein said amine salt is an aliphatic primary amine salt of a 1,2-benzenediolbis(monoalkylphosphate).

58. A composition in accordance with claim 51 wherein said oil-soluble amine salt is an oil-soluble amine salt of a 1,4-benzenediolbis(monohydrocarbylphosphate).

59. A composition in accordance with claim 58 wherein said amine salt is an aliphatic primary amine salt of a 1,4-benzenediolbis(monoalkylphosphate).

60. A composition in accordance with claim 51 wherein said oil-soluble amine salt is an oil-soluble amine salt of a 1,3-benzenediolbis(monohydrocarbylphosphate).

61. A composition in accordance with claim 60 wherein said amine salt is an aliphatic primary amine salt of a 1,3-benzenediolbis(monoalkylphosphate).

62. A composition in accordance with claims 61 wherein said amine salt is an oleyl amine salt.

63. A composition in accordance with claim 62 wherein said amine salt is an oleyl amine salt of 1,3-benzenediolbis(monopentylphosphate).

64. A composition in accordance with claim 62 wherein said amine salt is an oleyl amine salt of 1,3-benzenediolbis(monooctylphosphate).

65. A composition in accordance with claim 62 wherein said amine salt is an oleyl amine salt of 1,3-benzenediolbis(monodecylphosphate).

66. A composition in accordance with claim 51 wherein the monoamine is an aliphatic primary amine having 8 to 30 carbon atoms in the molecule and in which the aliphatic group of said amine is an alkyl group or an ethylenically unsaturated acyclic group having from 1 to 3 olefinic double bonds.

67. A composition in accordance with claim 66 wherein the monoamine has 9 to 20 carbon atoms in the molecule.

68. A composition in accordance with claim 51 wherein the monoamine is a tertiary alkyl primary amine.

69. A composition in accordance with claim 68 wherein the monoamine is a combination of tertiary alkyl primary amines having about 12 to about 14 carbon atoms in the molecule.

70. A composition in accordance with claim 68 wherein the monoamine is a combination of tertiary alkyl primary amines having about 16 to about 22 carbon atoms in the molecule.

* * * * *